(12) United States Patent
Ntziachristos et al.

(10) Patent No.: US 9,918,640 B2
(45) Date of Patent: Mar. 20, 2018

(54) METHOD AND DEVICE FOR MULTI-SPECTRAL PHOTONIC IMAGING

(75) Inventors: Vasilis Ntziachristos, Gräfelfing (DE); George Themelis, Unterföhring (DE)

(73) Assignee: Helmholtz Zentrum München Deutsches Forschungszentrum für Gesundheit und Umwelt GmbH (DE)

( * ) Notice: Subject to any disclaimer, the term of this patent is extended or adjusted under 35 U.S.C. 154(b) by 851 days.

(21) Appl. No.: 13/578,414

(22) PCT Filed: Nov. 15, 2010

(86) PCT No.: PCT/EP2010/006937
§ 371 (c)(1),
(2), (4) Date: Oct. 8, 2012

(87) PCT Pub. No.: WO2011/098101
PCT Pub. Date: Aug. 18, 2011

(65) Prior Publication Data
US 2013/0041267 A1 Feb. 14, 2013

Related U.S. Application Data

(60) Provisional application No. 61/304,008, filed on Feb. 12, 2010.

(30) Foreign Application Priority Data

Feb. 12, 2010 (EP) .................................. 10001478

(51) Int. Cl.
*A61B 5/00* (2006.01)
*A61B 1/00* (2006.01)
(Continued)

(52) U.S. Cl.
CPC ........ *A61B 5/0059* (2013.01); *A61B 1/00009* (2013.01); *A61B 1/00186* (2013.01);
(Continued)

(58) Field of Classification Search
CPC .... A61B 5/0059; A61B 5/0062; A61B 5/0071
See application file for complete search history.

(56) References Cited

U.S. PATENT DOCUMENTS 4,773,097 A 9/1988 Suzaki et al.
5,363,854 A 11/1994 Martens et al.
(Continued)

FOREIGN PATENT DOCUMENTS

CN 101057788 A 10/2007
EP 0 732 582 9/1996
(Continued)

OTHER PUBLICATIONS

Themelis, G. et al., "Real-Time Intraoperative Fluorescence Imaging System Using Light-Absorption Correction," *Journal of Biomedical Optics*, 2009, p. 64012-1 to 64012-9.
(Continued)

*Primary Examiner* — Rochelle Turchen
(74) *Attorney, Agent, or Firm* — DLA Piper LLP (US)

(57) ABSTRACT

An imaging device for medical imaging includes a light source device arranged to illuminate a sample under investigation with illumination light, a detector device arranged to collect a plurality of images including at least two sample light images backscattered by the sample in different spectral ranges, and at least one marker light image originating from at least one marker substance in the sample, and a processor device adapted to process the at least two sample light images and create at least one correction component, the processor device further adapted to correct the marker light image using the at least one correction component.

23 Claims, 7 Drawing Sheets

(51) Int. Cl.
  *A61B 1/04* (2006.01)
  *A61B 1/06* (2006.01)
  *G02B 21/16* (2006.01)

(52) U.S. Cl.
  CPC ............ *A61B 1/043* (2013.01); *A61B 1/0638* (2013.01); *A61B 5/0068* (2013.01); *A61B 5/0095* (2013.01); *G02B 21/16* (2013.01); *A61B 5/0064* (2013.01); *A61B 5/0073* (2013.01)

(56) References Cited

U.S. PATENT DOCUMENTS

| | | | |
|---|---|---|---|
| 2003/0187319 A1 | 10/2003 | Kaneko et al. | |
| 2005/0203423 A1 | 9/2005 | Zeng et al. | |
| 2007/0178602 A1 | 8/2007 | Wolleschensky et al. | |
| 2008/0039695 A1 | 2/2008 | Takaoka et al. | |
| 2008/0051665 A1 | 2/2008 | Xu et al. | |
| 2008/0123083 A1 | 5/2008 | Wang et al. | |
| 2008/0192248 A1* | 8/2008 | Carver | A61B 5/0068 356/301 |
| 2008/0266564 A1 | 10/2008 | Themelis | |
| 2008/0312540 A1 | 10/2008 | Ntziachristos | |
| 2009/0207412 A1* | 8/2009 | Mahmood | A61B 5/0059 356/406 |
| 2012/0053429 A1 | 3/2012 | Trepagnier et al. | |

FOREIGN PATENT DOCUMENTS

| | | |
|---|---|---|
| EP | 2 108 300 | 10/2009 |
| JP | 60-256443 A | 12/1985 |
| JP | 5-293108 A | 11/1993 |
| JP | 2001-137173 | 5/2001 |
| JP | 2003-164414 | 6/2003 |
| JP | 2003-522579 | 7/2003 |
| JP | 2003-290126 | 10/2003 |
| JP | 2006-527858 | 12/2006 |
| JP | 2008-43494 | 2/2008 |
| JP | 2008-61969 | 3/2008 |
| JP | 2008-261885 | 10/2008 |
| JP | 2008-264578 | 11/2008 |
| WO | 00/42910 | 7/2000 |
| WO | 2008/062354 | 5/2008 |
| WO | 2010/009747 A1 | 1/2010 |

OTHER PUBLICATIONS

Andersson-Engels, S. et al., "Medical Diagnostic System Based on Simultaneous Multispectral Fluorescence Imaging," *Applied Optics,* 1994, vol. 33, No. 34, pp. 8022-8029.

Ntziachristos, V. et al., "Looking and Listening to Light: the Evolution of Whole-Body Photonic Imaging," *Nature Biotechnology,* 2005, vol. 23, No. 3, pp. 313-320.

Search Report of Chinese Official Action dated Mar. 5, 2014 of corresponding Chinese Application No. 2010800661339.

* cited by examiner

METHOD AND DEVICE FOR MULTI-SPECTRAL PHOTONIC IMAGING

RELATED APPLICATIONS

This is a §371 of International Application No. PCT/EP2010/006937, with an international filing date of Nov. 15, 2010 (WO 2011/098101 A1, published Aug. 18, 2011), which is based on European Patent Application No. 10001478.6, filed Feb. 12, 2010, and U.S. Patent Application No. 61/304,008, filed Feb. 12, 2010, the subject matter of which is incorporated by reference.

TECHNICAL FIELD

This disclosure relates to an imaging device, in particular for medical imaging, like a multi-spectral photonic system, which offers significantly better imaging accuracy compared to conventional techniques, for surface and sub-surface imaging of a sample including at least one marker substance. Furthermore, this disclosure relates to an imaging method, in particular for medical imaging of a sample including at least one marker substance, e.g., a human or animal or part thereof. Preferred applications are present in medical imaging and in particular in creating diagnostic images or images used for guiding interventional procedures.

BACKGROUND

Photonic imaging is an ideal modality for biomedical diagnostics since it relates directly to a physician's vision and offers highly attractive characteristics, including use of non-ionizing radiation which does not damage the tissue, high flexibility in contrast mechanisms, portability, small form factor and real-time image acquisition. Healthy and diseased tissues exhibit differences in several properties such as structural, compositional, metabolic, molecular and structural. Local or systemic administration of agents with specificity to cellular and subcellular tissue and disease biomarkers could alter the optical properties of healthy and diseased tissue in a different way resulting in visualization of lesions with high contrast with the background healthy tissues. Recent studies indicate that the use of externally administered fluorescent probes is a highly promising approach since fluorescence signals can provide high contrast. For example, engineered probes can be very sensitive and specific in cancer detection by targeting specific molecular features of carcinogenesis and tumor lesions.

The need to efficiently detect the signal from molecular probes led to the development of several imaging methods and technologies in the last decade. Nevertheless, imaging methods used in practice suffer from limitations related to a) performance and b) convenience in use especially in clinical environments.

The imaging performance in resolving superficial fluorescence activity can be compromised by three major parameters: spatial variation in tissue optical properties, depth of the fluorescence activity and tissue auto-fluorescence. The dependence of signal intensity, e.g., fluorescence, on these parameters can limit both the contrast and the overall accuracy of uncorrected simple "photographic" or "video" methods. This can be better understood by considering, for example, that a dark, bloody area, significantly attenuates light intensity over a less absorbing region, an effect that can lead to false negatives. Similarly a non-absorbing area may show as probe rich compared to a dark region even at very moderate amounts of molecular probe. This can lead to false positives. Similar false positives or false negatives can be also generated as a function of the depth of the fluorescence lesion since light intensity non-linearly and strongly attenuates as a function of depth, i.e., light propagation in tissue. Therefore, unless one corrects for the variation in fluorescence signal intensity due to the variation of optical properties, variation of depth or auto-fluorescence raw images of tissue can be inaccurate or contain undesired artifacts. These effects have been noted in the past (e.g., see Ntziachristos et. al. Nature Biotechnology 2005; 23:313-320).

Systems that utilize imaging at multiple wavelengths have been developed to differentiate auto-fluorescence from a fluorochrome of interest. Similarly, variation of the intensity due to tissue optical properties and depth is typically corrected in tomographic systems.

On the other hand, further systems that show the potential to overcome the abovementioned limitations in performance are not suitable for clinical use due to poor functionality characteristics. For example, scanning multispectral systems can provide high spectral resolution but require time for scanning and therefore are not suitable for moving objects, i.e., real-time imaging operation. Therefore, they are not suitable for use on tissues moving due to breathing or heartbeat. Moreover, information generated by the images is not provided in real time and therefore such methods are impractical for scanning large tissue areas for lesions, zoom and focus on suspicious areas during examination and, last but not least, cannot be used for interventional procedures such as real time surgical guidance for lesion excision.

Overall, currently no medical photonic imaging system exists that accounts for the effects of light propagation and interaction with tissue in real-time to lead to accurate clinical imaging systems, for example, intra-operative imaging systems.

Tissue lesions, e.g., cancer, exhibit alterations in the tissue molecular, structural, functional and compositional characteristics. The use of targeting probes, e.g., molecular probes, has the potential to provide significant contrast between healthy and diseased tissue. Especially, with recent advances in genomics, proteomics and nanotechnology, new probes conjugated with appropriate optical markers, e.g., a fluorescent molecule or a photo-absorbing nano-particle, enable easier and more accurate detection of tissue structural, functional and compositional properties which could lead to non-invasive in vivo diagnostics. Ideally, an imaging modality able to capture those differences in optical signals and thereby detect and identify tissue lesions in real time could significantly increase our diagnostic, real-time guidance and interventional imaging capabilities.

Although several experimental methods have proven the potential of this approach, none of them exhibits sufficient performance for clinical use. The main limitations are: due to high complexity and inhomogeneity of biological tissues, photons undergo multiple and complex interactions with the tissue resulting in alterations to the measured signal. Correction of the measured signals requires a complex model that contains aspects of the tissue optical properties and/or geometrical characteristics. Reliable measurement of tissue optical properties requires fast acquisition and processing of a large amount of information. Existing imaging methods and technologies are limited as to the amount of information they can capture and correction they can offer.

Clinical applications such as surgical guidance require real time diagnostic or pathology feedback. In other words, signal capturing, processing and rendering of diagnostic result should be done in real time. Existing methods are limited by a tradeoff between analytical capabilities and speed.

US 2008/0312540 A1 discloses a system and method providing normalized fluorescence epi-illumination images and normalized fluorescence transillumination images for medical imaging. Normalization is obtained by combining an intrinsic image, like, e.g., a reflection image, and an emitted light image, like, e.g., a fluorescence image, collected at the sample. This conventional technique has limitations in practical applications, in particular due to the time needed for collecting images with multiple spectral ranges using changing optical filters or filter wheels, the duration of image data processing and a limited image quality. Furthermore, this technique has a restricted capability of providing diagnostic images since it only partially accounts for optical property changes, i.e., it accounts for absorption changes but not scattering changes.

It could therefore be helpful to provide an improved imaging device, in particular for multi-parametric real-time medical imaging, capable of avoiding disadvantages of conventional techniques. Furthermore, it could be helpful to provide an improved imaging method, in particular for collecting and providing photonic images for biomedical imaging with improved accuracy, being capable of avoiding disadvantages of conventional techniques.

SUMMARY

We provide an imaging device including (a) a light source device arranged to illuminate a sample under investigation with illumination light, (b) a detector device arranged to collect a plurality of images including at least two sample light images backscattered by the sample in different spectral ranges, and at least one marker light image originating from at least one marker substance in the sample, and (c) a processor device adapted to process the at least two sample light images and create at least one correction component, the processor device further adapted to correct the marker light image using the at least one correction component.

We also provide an imaging method including illuminating a sample under investigation with illumination light generated with a light source device, collecting at least two sample light images from sample light backscattered by the sample, collecting at least one marker light image from marker light generated by at least one marker substance in the sample in different spectral ranges, and processing the sample and marker light images and rendering at least one corrected marker light image based on the at least two sample light images and the at least one marker light image.

BRIEF DESCRIPTION OF THE DRAWINGS

Further details and advantages are described in the following with reference to the attached drawings, which show.

DETAILED DESCRIPTION

We provide an imaging device which comprises a light source device arranged for illumination of a sample under investigation with illumination light, and a plurality of detectors arranged for collecting multiple different images of the sample. The detectors include at least one multi-spectral sample light camera capable of sensing sample light coming from the sample, e.g., backscattered (reflected and/or back-emitted) and generated by the sample in different spectral ranges, and collecting at least two sample light images of the sample in the different spectral ranges, and at least one marker light camera capable of simultaneous sensing marker light generated by at least one marker substance in the sample and collecting marker light images of the sample. The at least two sample light images are used for calculating at least one correction component. The marker light image is corrected using the at least one correction component which is a correction image or another signal including information relevant for correction of the marker light image. Preferably, the sample and marker light images with the different spectral ranges of light detection are collected simultaneously, i.e., at the same time. Time delay as it may occur with the conventional technique, e.g., with changing optical filters, is avoided. The cameras utilized can be optical cameras including light-sensitive chips, e.g., a Charged Coupled Device (CCD) sensor or a CMOS-sensor.

To collect the sample and marker light images simultaneously, our imaging device includes a light splitting imaging optic which is configured for imaging light from the sample onto the detectors. The sample light is relayed onto the at least one sample light camera, while the marker light is relayed onto the at least one marker light camera. Both of the sample light and the marker light are collected simultaneously, thus allowing a real time processing of the multiple different images of the sample.

Furthermore, our imaging device includes a processor device being adapted for processing the sample and marker light images in parallel and rendering at least one corrected image based on the at least one marker light image and the sample light images. Preferentially, the at least one corrected image is computed and rendered in a real-time mode. Providing at least one corrected image in real-time mode comprises the representation of the at least one corrected image on a display at one time with the image collection or with a delay after the image collection such that the delay is negligible in consideration of the time scale of sample changes or treatment steps.

Providing at least one corrected image in real-time mode also may include providing an image sequence (video sequence) of corrected images. As an example, the processor device can be configured to generate a video sequence of the at least one marker light image, at least one of the sample light images, the at least one corrected image, or the optoacoustic image or a combination thereof.

We also provide an imaging method which preferably is conducted using the imaging device. The imaging method comprises the steps of illuminating a sample under investigation with illumination light generated with a light source device, collecting sample light images created by sample light backscattered, in particular reflected, by the sample in the different spectral ranges and collecting at least one marker light image created by marker light generated by at least one marker substance in the sample, wherein the sample and marker light images are collected using a light splitting imaging optic, at least one multi-spectral sample light camera and at least one marker light camera, and processing the sample and marker light images and rendering at least one corrected image based on the sample light images and the at least one marker light image in a real-time mode.

Preferably, the sample is a biological object, in particular a human or animal body or a part thereof. In particular, the sample comprises biological tissue or a part thereof. Accordingly, the device/method is preferably used for medical imaging.

Generally, the sample light collected with the sample light camera is the portion of the illumination light reflected (scattered) by the surface and sub-surface layers of the sample. Accordingly, the sample light includes contributions of the background body of the sample and possibly of the at least one marker substance distributed in the sample. The term "sample light image" refers to an incident light image of the sample, like a diffusive reflection image, or a color image, obtained by imaging light at the surface of the sample onto the sample light camera. On the other hand, the marker light refers to light specifically emitted or reflected by the at least one marker substance.

Sensing exclusively the marker light would allow a strict discrimination between the sample background light and the marker light and an assignment of the marker light to certain topographic properties of the sample, e.g., to recognize suspicious tissue regions. This discrimination is difficult due to the broadband characteristics of the sample background and marker substance. With the collection of multiple sample and marker light images in different spectral ranges, this discrimination can be essentially facilitated. As the sample and marker light image collection is performed simultaneously and the corrected image is calculated in real-time, an essential advantage is obtained in comparison with conventional medical imaging methods.

Advantageously, we provide a method and a device for photonic medical imaging of marker substance which can offer accurate, quantitative imaging of surface and subsurface tissues and tissue markers. This performance is in contradistinction to the current state of the art that not offering accurate performance can lead to false negatives and false positives. In addition, our methods can enable this accurate performance in real-time collection and processing of multispectral data. The real-time system and method is capable of molecular imaging as it associates with the specific and accurate visualization of administered marker substances with specificity to certain healthy and diseased tissue marker substances.

For the preferred application in medical imaging, we provide three steps of administration of one or more contrast agents or probes (marker substances), e.g., molecular probes, multispectral optical imaging, optionally with optoacoustic imaging, and processing of captured images for real time display of corrected information. The administration step is provided as an optional feature of the method. It can be omitted if the sample already includes the at least one marker substance for natural reasons or due to a previous treatment. The at least one corrected image obtained with the imaging method is also called diagnostic image. The term "diagnostic image" refers to the fact that the image can be used for finding a diagnosis, e.g., by a physician and/or by a subsequent image evaluation or identify with high specificity a problematic or suspicious lesion to lead to efficient guidance and intervention, for example, an intervention with therapeutic intend. As an example, the diagnostic image may include a map of the sample highlighting various sample conditions. Similarly, the diagnostic image can be used to guide surgical intervention or endoscopically administered biopsies and other surgical procedures.

The term "marker substance" refers to any molecule which specifically binds to a certain target in the sample, like target tissue, target cells or certain cell components, like proteins, and which exhibits an interaction with light (UV, VIS and/or IR wavelength ranges) resulting in a specific absorption and/or fluorescence. The concept of use of a marker substance is to high-light one or more tissue characteristics which are altered at a presence of a disease. The marker substance is also called biomarker, probe or contrast agent. It is selected depending on the binding properties and the spectral properties thereof. In particular, the marker substance is selected so that it targets and reveals a molecular, structural, functional or compositional feature of the tissue which specifically changes in a gradual manner during the disease progress. The presence of the marker substance preferably alters the optical properties of the tissue, e.g., fluorescence or absorbance in a way that the detected optical signal could even reveal the presence or progress of the disease. The sample includes one or more marker substances. If multiple different marker substances are provided, they preferably have different spectroscopic properties.

A disease like cancer is known to cause several tissue alterations and the probes used as a marker substance are in general designed to highlight one of those alterations, e.g., metabolic activity. Nevertheless, diseases like cancer do not always express the same characteristic changes and therefore, the probes inherently exhibit low sensitivity. Inversely, in other cases some non-diseased tissues might also mimic one of the disease characteristics reducing thereby the probe specificity. Besides cancer, interventions associated with vascular, intravascular, neuronal, cardiac, reconstructive and other diseases and indications are also considered.

With the available specific and sensitive marker substances such as molecular probes, it is possible to provide an excellent overall performance and clinical outcome using the method. Moreover, combined use of multiple probes may be preferred in terms of further increasing the information obtained for decision making during guidance and intervention or the diagnostic ability since the detection of a disease can then be based on several features that characterize the disease rather than a single feature. Additionally, the combined use of multiple probes and other chromophoric agents such as non-specific fluorescence dyes could additionally be utilized to correct for potential inhomogeneities in local blood perfusion which could otherwise affect the local delivery of the probes and thereby introduce measurements.

Advantageously, the method can be conducted with various types of images. Our detectors are adapted to collect at least two image types of a color image, a fluorescence image, a reflectance image and/or an excitation image. Preferably, each of the detectors is provided with at least one camera filter adapted to the image type to be collected.

The marker light is light generated in response to the illumination by at the least one marker substance. Intensity, spectral composition and geometric distribution of the marker light is determined by the specific interaction of the illumination light with the at least one marker substance and the distribution thereof in the sample. Multiple variants exist for adapting the at least one marker light camera for efficiently sensing the marker light in different spectral ranges. Preferably, the at least one marker light camera comprises two or more camera fields being sensitive in the different spectral ranges. A light splitting camera optic is arranged for imaging portions of the light created by the sample onto the at least two camera fields. Particularly preferred is a variant, wherein the at least one marker light camera is provided for simultaneous sensing the marker light in at least two different spectral ranges. In this case an essentially improved specific detection of the marker substance distribution and discrimination from the background sample light can be obtained.

The at least two camera fields may comprise at least two separate light-sensitive chips, e.g., CCD chips and/or at least two independently sensitive areas within one common light-sensitive chip, e.g., CCD chip. This allows a flexible adaptation of the imaging device to the requirements of a practical application where different signals collected utilize different signal strengths and different dynamic ranges. Preferably, the sensitivity of one or more of the independently light-sensitive field is automatically adapted, through variable attenuation or amplification of the sample signals collected or the corresponding electrical signals generated. Preferably, each of the at least two camera fields is provided with a field filter being adjusting a spectral sensitivity range of the respective camera field. If changeable field filters are provided, the flexibility even can be improved.

Advantageously, the illumination light can be designed in terms of geometric, temporal and/or spectral properties for adapting the illumination light to sample properties (including marker substance properties) and image types to be collected. To this end, the light source device preferably includes at least one illumination light conditioning device adjusting at least one of a spectral characteristic, a temporal characteristic, a polarization, a direction and a light field shape of the illumination light. If the illumination device includes multiple light sources, for each of them a specific illumination light conditioning device can be provided. Preferably, the illumination light conditioning device comprises at least one of a spectral filter, a polarization filter, an illumination optic and a bundle of optical fibers.

Preferably, the optical imaging can be combined with opto-acoustic sensing. Opto-acoustic is a promising modality that combines advantages of optical imaging, i.e., high optical contrast mechanisms and tomographic methods, i.e., high penetration depth. The combination of optical and optoacoustic sensing is ideal since both modalities can utilize the same marker substances. Therefore, an opto-acoustic imaging device is arranged for collecting a multi-spectral opto-acoustic image of the sample. The opto-acoustic imaging device is capable of collecting at least opto-acoustic data, but preferably an opto-acoustic image of the sample.

Accordingly, our device can be provided as an opto-acoustic device, offering real-time collection and correction capability, i.e., as a combination of the optical, CCD-based device and the opto-acoustic device. In this case, the CCD-based device used for guidance and large field of view detection and the opto-acoustic device used for resolving with high resolution contrast from suspicious regions found on the CCD-based device. A similar practice can also utilize a portable confocal or multi-photon microscope imaging system.

The processor device of the imaging device is an important feature providing the capability of real time imaging of the sample, where the images produced in real time in particular are corrected images that account for features that can lead to artifacts (i.e., false positive or false negative readings) that may be present in the raw images. Preferably, the processor device includes at least one of Field Programmable Gate Arrays and Graphic Processing Units. As an advantage, those types of processors are commercially available at relatively low prices and provide the ideal solution for dedicated real time data processing.

Optionally, a control device can be provided additionally to the processor device. The control device can be configured for at least one of the following functions. Firstly, it can control the light source device, the detectors and/or the processor device. Secondly, the control device can be provided with a display device displaying the at least one sample light image, at least one of the marker light images, the at least one corrected image and/or the opto-acoustic image. Finally, the control device may be connected with an administering device which configured for introducing the at least one predetermined marker substance into the sample. The processor device and the control device can be implemented within a common computer unit.

The flexibility of the imaging device can be further improved if the detectors are arranged with a modular structure having a plurality of couplings each of which being arranged for accommodating one of the detectors. Advantageously, this allows a simple adaptation of the imaging device to the requirements of a particular application.

Further preferably, the step of rendering the at least one corrected image includes an image data correction procedure. "Image data correction" refers to preferentially and independently modifying the information contained to each pixel of a "final image" also presented to the systems operator so that predetermined features of the image are improved and convey to the operator more accurate information.

The image data correction applied is based on the multi-parametric data collected in real-time, and may also contain a-priori knowledge, in the form of information stored in the image processing device prior to the real-time measurement. Correspondingly "image data correction" also refers to change the intensity in the pixels of the image corrected and subsequently projected so that the resulting image more accurately reflects the actual marker bio-distribution in the field of view of the image. The image data correction therefore may contain any of steps that improve the intensity in each image 1) from the effects of contamination of marker signals with endogenous tissue signals, such as auto-fluorescence signals, 2) from the effects that the depth of the marker location has on the marker signal collected, and/or 3) the effect that the tissue optical properties have on the marker signal collected. For example, the effect that a strong absorber co-localized with a marker fluorochrome has on the intensity recorder from the marker fluorochrome. Particular examples of image data correction are described below.

Preferred example are described in the following with particular reference to the optical and opto-acoustic set-up and data processing structure provided for obtaining multi-spectral photonic images in real time. Details of selecting suitable marker substances, preparing a sample, like introducing at least one marker substance type into the sample, designing the imaging optics, in particular with regard to focusing and magnification properties, operating the at least one light source, detectors and optionally further sensors, like an opto-acoustic sensor and image processing techniques are not described here as far as they are known from prior art, in particular from conventional photonic systems for medical imaging. Furthermore, the imaging devices presented in the figures can be implemented in different ways depending on the specific needs of an application.

Figure 1:
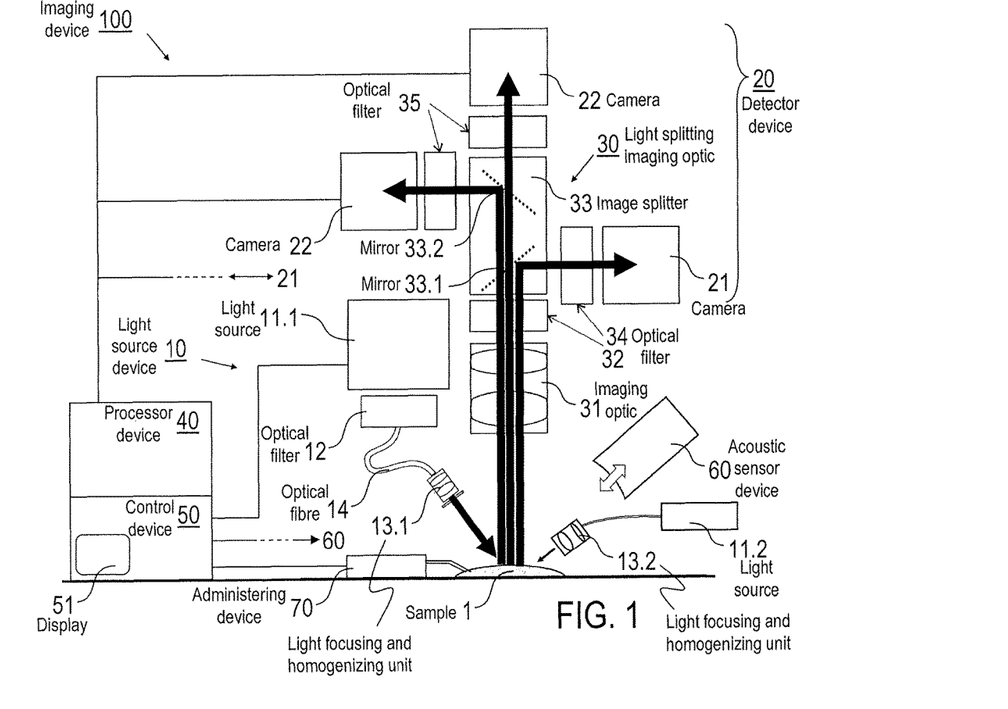
FIG. 1: a schematic illustration of our imaging device.

FIG. 1 illustrates features of preferred example of the imaging device 100 which comprises a light source device 10, a detector device 20 with detectors 21, 22, a light splitting imaging optic 30 and a processor device 40. Optionally, additionally a control device 50, an opto-acoustic sensor device 60 and/or an administering device 70 can be provided. The imaging device 100 is configured to image a sample 1 with the imaging method. The sample 1 is, e.g., a biological sample, like a human or animal body or a part thereof. For in vitro investigations, the sample 1 is arranged on a carrier, while with an in vivo investigation (see FIG. 4) the sample 1 is a region of investigation included in the body of the proband (patient).

The light source device 10 comprises two light sources 11.1, 11.2, an optical filter 12 and light focusing and homogenizing units 13.1, 13.2, which are arranged to illuminate the sample 1 with illumination light. The components 12 and 13.1 being connected via an optical fibre 14 and the component 13.2 provide illumination light conditioning devices, which are adapted for adjusting the spectral characteristic (in particular with the optical filter 12) and the polarization, direction and/or light field shape of the illumination light (in particular with the light focusing and homogenizing units 13.1, 13.2). Additionally or alternatively, the illumination light conditioning device may be provided with a temporal illumination control, like a shutter, a switching device or a light source control (not shown).

While the method can be implemented with a single light source, like, e.g., a laser source, the light source device 10 preferably comprises multiple light sources, which provide advantages in terms of providing illumination light with predetermined spectral and temporal characteristics. As an example, the light source device may comprise at least one broadband light source 11.1, e.g., a white light tungsten bulb, a halogen lamp or a broadband LED, or at least one narrowband light source 11.2, like, e.g., a narrowband laser or LED. When multiple narrowband light sources are utilized, the different bands can be employed to excite at least one marker substance in tissue, which can be employed to visualize multiple markers simultaneously or correct for the effects of depth, since different spectral bands can probe different depths. With the provision of multiple light sources, the illumination light conditioning device comprises multiple filters, focusing and homogenizing components. In terms of temporal characteristics, the light source can be continuous (CW), pulsed or intensity modulated. The light from each light source 11.1, 11.2 could be delivered from each source directly to the sample or the output of all light sources could be combined and delivered by a single optical arrangement, e.g., fiber optic bundles or lens.

The light from the sources, each one separately or all together could be filtered to achieve the necessary spectral characteristics. As an example, IR light might be filtered out from white light indented for color imaging so that there is no crosstalk with the IR fluorescence signal detection. Moreover, the use of polarizers at the illumination and imaging optical paths could minimize effects of specular reflection.

The detector device 20 comprises three cameras 21, 22 arranged to collect sample light and marker light, respectively. The sample light and the marker light is relayed from the sample 1 to the cameras 21, 22 using the light splitting imaging optic 30, which comprises an imaging optic 31 collecting the light from the sample 1, multiple optical filters 32, 34, 35 being arranged to adjust spectral features of the sample light and marker light, and an image splitter 33 separating the light paths from the imaging optic 31 towards the cameras 21, 22. The optical filters 32, 34, 35 (camera filter) can comprise filter wheels loaded with appropriate band pass filters, which enable the selection of the imaging spectral band for each camera independently. The image splitter 33 comprises two semi-transparent plane mirrors 33.1, 33.2, wherein, as an example, the first mirror 33.1 is a dichroic mirror that reflects visible light towards the sample light camera 21 and has 10% reflectance and 90% transmittance, while the second mirror 33.2 has 5% reflectance and 95% transmittance.

The sample light camera 21 is arranged to collect the sample light image of the sample 1. The spectral characteristic of the sample light is adjusted with the optical filter 34, which, e.g., suppresses spectral ranges of marker substance fluorescence or passes visible light. The sample light camera 21 includes a camera sensor, like, e.g., a CCD sensor as known from conventional photographic cameras. The sample light camera 21 is connected with the processor device 40, wherein the sample light image is processed (see below).

The cameras 22 have a more complex structure as they are arranged for sensing marker light in different spectral ranges simultaneously in real time. To this end, the marker light cameras 22 have a structure as further illustrated in FIGS. 2 and 3. The marker light cameras 22 are connected with the processor device 40, wherein the marker light images are processed in parallel together with the sample light image to render at least one corrected image in real time. Details of image processing are discussed below with reference to FIGS. 5 and 6. Alternatively, one of the cameras in 22 may be arranged to detect a third light such as auto-fluorescence, or a sample light, at one or more spectral bands, as described in FIG. 1 and FIG. 3, giving flexibility in the utilization of the proposed example.

The light splitting imaging optic 30 is arranged in a casing (not shown) shielding the light paths from the sample 1 to the cameras 21, 22. As an example, the casing can be structured with a tube shape as it is known from microscopes. The detectors 21, 22 are connected with the casing having a modular structure with a plurality of couplings each of which being arranged for accommodating one of the detectors.

Figure 2:
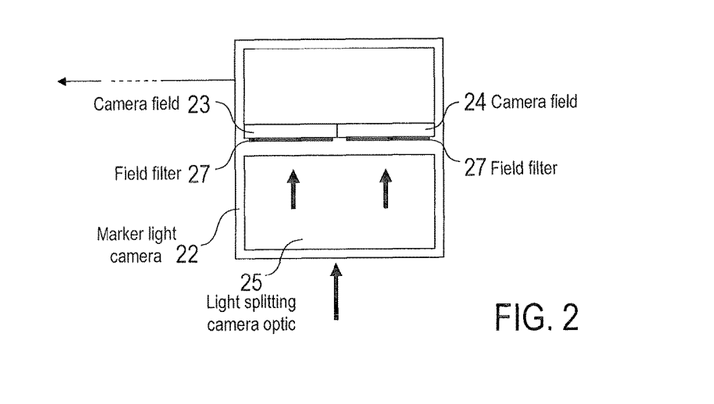
FIGS. 2 and 3: schematic illustrations of detectors used in the imaging device.
Figure 3:
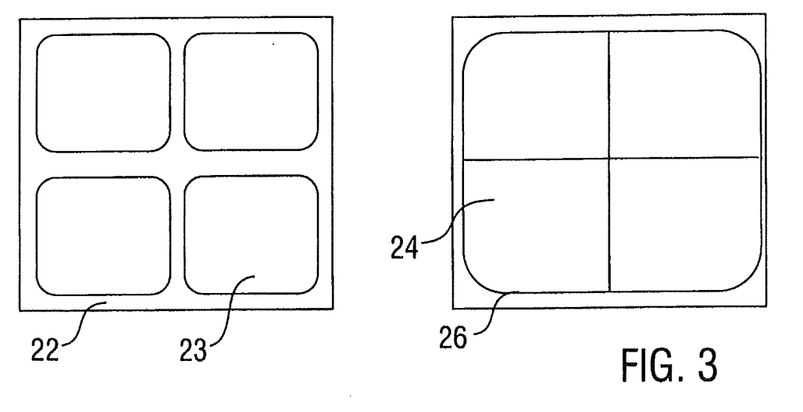

FIG. 2 schematically illustrates a sectional view of a marker light camera 22, which comprises at least two camera fields 23, 24 each with a field filter 27. Furthermore, the marker light camera 22 comprises a light splitting camera optic 25, which is adapted to split marker light relayed from the light splitting imaging optic 30 (see FIG. 1) towards the camera fields 23, 24. On each of the camera fields 23, 24, a complete image of the sample (or region of interest) is created. The light splitting camera optic 25 comprises a combination of mirrors and/or prisms as it is known from conventional image splitters.

The camera fields may comprise separate CCD chips 23 as schematically illustrated in FIG. 3A and/or sensitive areas 24 of one common CCD chip 26 as illustrated in FIG. 3B. In the first case, each of the CCD chips 23 is connected with the processor device 40 for transferring the marker light image data. In the second case, the common CCD chip 26 is connected with the processor device 40, wherein image data belonging to the different sensitive areas 24 are separated with a data processing in the processor device 40.

The processor device 40 (FIG. 1) is configured to process the sample and marker light images in parallel and rendering at least one corrected image based on the at least one marker light image and the sample light images in a real-time mode. Real time processing and rendering of the imaging data is particularly important for the clinical use of a diagnostic system. Nevertheless, this real time processing is quite demanding and conventional computer CPUs may have an insufficient performance. Therefore, preferably, the processor device 40 has a separate processor dedicated to image data processing. Such processors could be Field Programmable Gate Arrays (FPGAs) and Graphics Processing Units (GPUs).

According to FIG. 1, the control device 50 is connected with the processor device 40 and with the cameras 21, 22. The connection with the cameras 21, 22 can be provided directly or via the processor device 40. Furthermore, the control device 50 is connected with the light source device 10, the opto-acoustic sensor device 60 and the administering device 70. Thus, the control device 50 is capable for controlling the complete operation of the components of the imaging device 100. The control device 50 is provided with a display 51 illustrating operation conditions of the imaging device 100 and/or images collected with the camera device 20 and/or calculated with the processor device 40.

The opto-acoustic sensor device 60, including, e.g., an ultrasonic array, is arranged to collect an opto-acoustic image of sample 1 simultaneously or guided by the collection of the sample and marker light images. The opto-acoustic modality could provide complementary information, e.g., about the lesion morphology in deeper layers of the tissue or resolve the same marker with depth resolution and as a function of depth, in particular when using multispectral optoacoustic tomography (MSOT). To this end, the opto-acoustic sensor device 60 is configured to subject the sample 1 to one or multiple excitation light pulses and for collect a mechanical wave response created in the sample 1 as it is known from conventional opto-acoustics. The excitation light pulse can be created with one of the light sources 11.2 or, in other words, one light source 11.2 of the light source device 10 can be integrated in the opto-acoustic sensor device 60.

The imaging system of FIG. 1 facilitates an optical construction that splits the light collected by the imaging optic 31 into multiple imaging channels. The light splitting is performed such that each of the imaging channels measures one or more spectral bands of fluorescence and/or reflectance light. This light splitting example is designed to minimize the crosstalk between the imaging channels and maximize the optical throughput.

Each imaging channel utilizes additional optical filtering (filters 34, 35) to ensure the purity of the measured signal. Each of the cameras 21, 22 can be conventional monochrome or color, multispectral, time-resolved or intensity modulated. The light splitting example can optionally utilize one or more relay lenses to form an image of the correct size and magnification on each of the camera sensors. Light splitting can be performed by any combination of partially reflecting mirrors or prisms, dichroic or polichroic mirrors and polarization splitters. For the imaging optic 31 can be used any imaging example that can collect light and form an image such as refractive and/or reflective (catoptrics) elements.

In a practical example, the imaging device 100 of FIG. 1 is configured for intraoperative fluorescence imaging. It enables simultaneous image capturing of color, fluorescence and intrinsic (excitation spectral band) imaging for marker substances consisting of IR-fluorescent probes, e.g., Cy5.5 and AlexaFluor750. For this application, the sample light camera 21 is a color camera coupled with a filter for the visible wavelength range to ensure only visible photons will be detected. The halogen lamp light source 11.1 with the infrared light filtered out is used for white light illumination of the sample 1 for the purpose of color imaging. The second light source 11.2 is a laser for the excitation of fluorophores. The laser can be a diode laser at the wavelength of 673 nm for the excitation of Cy5.5-labeled probes or a 750 nm for the excitation of AlexaFluor750-labeled probes. For the white light source 11.1 and the laser 11.2, the light is delivered to the sample 1 (e.g., tissue) through a fiber optic bundle and a multimode fiber respectively to a collimator and a diffuser (13.1, 13.2) for beam expansion and uniform illumination. Alternatively, one of the cameras 22 collects intrinsic tissue fluorescence, or fluorescence coming from tissue at another spectral band than the one that the first fluorescence camera is operating in so that it can derive and correct for auto-fluorescence or measure a second target marker fluorochrome or intrinsic tissue fluorochrome or chromophore, for example, at least one form of hemoglobin.

Light from the sample 1 under examination is collected using a zoom lens of the imaging optic 31. Alternative to the zoom lens could be used any optical imaging system such as endoscope or microscope. Two linear polarizers with perpendicular polarization axes can also be employed at illumination and imaging light paths to eliminate specular reflection. The primary image of the sample 1 formed by the zoom lens falls at the focal plane of each relay lens group of three imaging channels.

FIG. 1 is a schematic representation of the imaging platform. The imaging device 100 of FIG. 1 is capable of capturing any combination of the following:
  color image so that a surgeon will be able to recognize an area under examination,
  multispectral fluorescence images,
  multispectral reflectance images, and
  opto-acoustic signals.

All this optical information captured will be used to calculate images of diagnostic value as outlined below.

Figure 4:
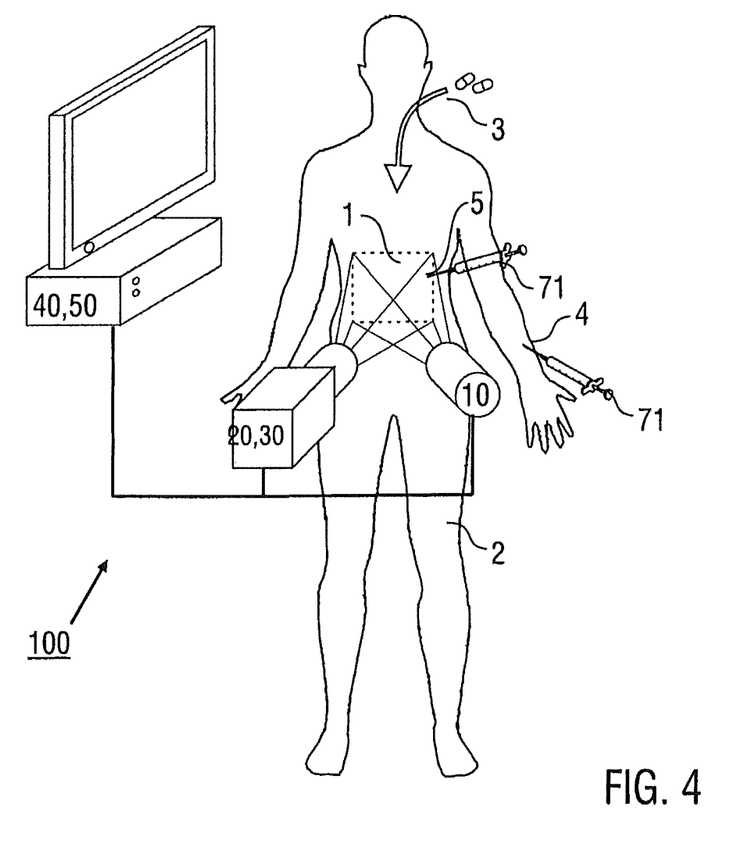
FIG. 4: a schematic illustration of a preferred application of the imaging device.
Figure 6:
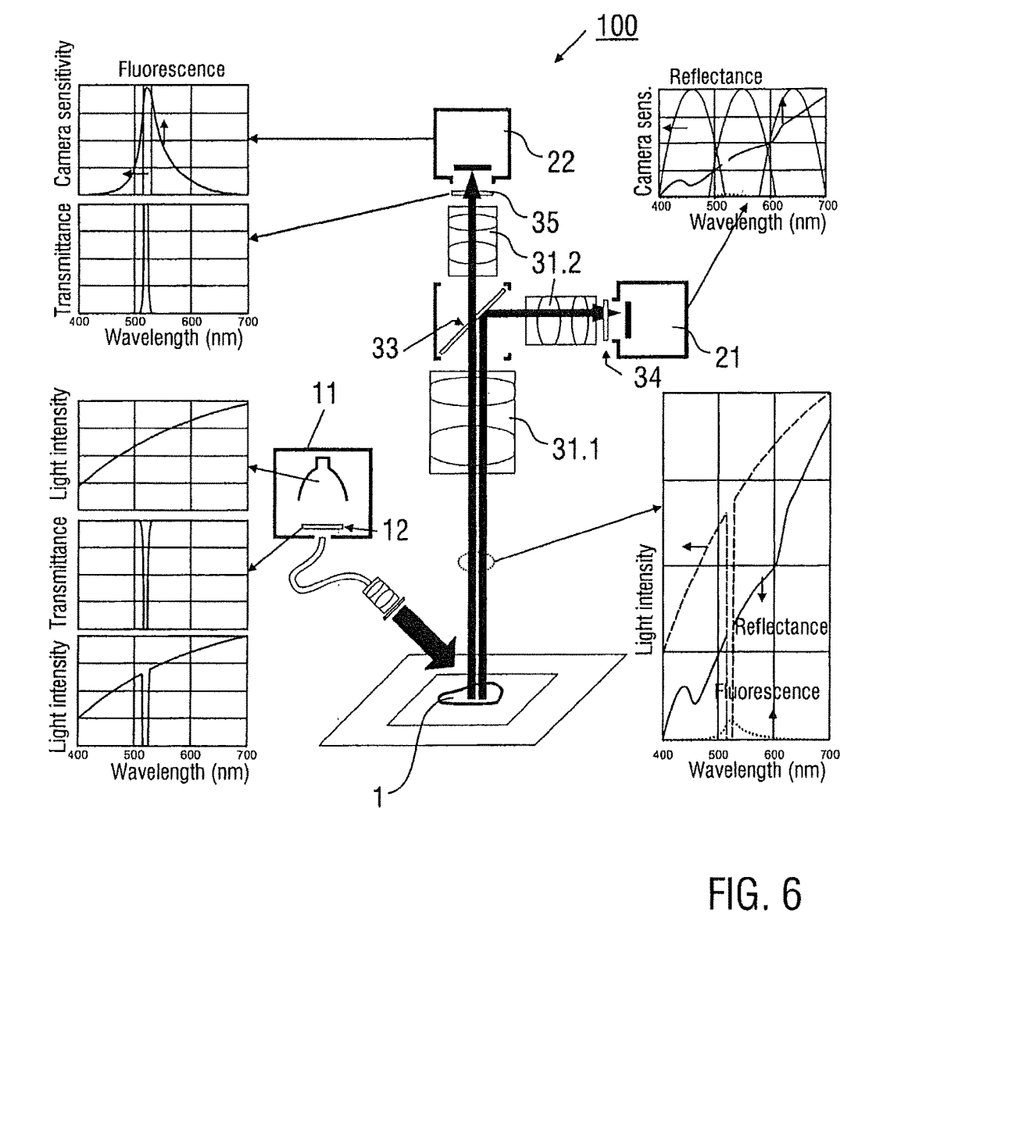
FIG. 6: a schematic illustration of a practical application of the device.

In this example, the imaging device 100 employs three imaging channels but in the exact same way it could be implemented with less (two) or more imaging channels, as shown in FIG. 6. Intrinsic images in a two-camera configuration can be provided by processing the color image to convert it to a near-infared attenuation map, based on spectral information relating visible and near-infrared spectra already stored in the processing device. Furthermore, while features are described above with exemplary reference to an optical set-up, which has a structure similar to an optical microscope, it is emphasized that the implementation is not restricted to this illustrated structure, but rather possible with more compact apparatuses. In particular, the imaging optics, image splitting optics and cameras can be integrated within one single compact casing or within two casings as illustrated in FIG. 4. It is even possible to miniaturize the imaging device such that it can be used for conventional medical imaging techniques, like, e.g., endoscopy.

FIG. 4 shows application of the technique for medical imaging, wherein the sample 1 is a part of a human 2. The sample 1 (region of investigation) is, e.g., a surface region or a sub-surface tissue region, like a subcutaneous tissue region imaged during a surgical operation and/or using an endoscopy instrument. The imaging device 100 comprises the illumination device 10, the light splitting imaging optic 30, the detector device 20 and the processor and control device 40, 50. Reference numeral 71 indicates parts of an administering device 70, which is adapted to introduce at least one marker substance to the sample 1 and which includes a marker substance reservoir, a supply conduit (like a syringe needle) and a drive unit. The administering device 70 can be adapted for an automatic operation controlled by the control device 50 (see FIG. 1).

FIG. 4 illustrates that the method fundamentally consists of three parts, namely 1) an administration of a diagnostic probe (including the at least one marker substance, in particular at least one fluorescence agent), either systemically (3, 4) or locally (5), 2) operating the imaging system, and 3) real time processing and displaying. Thus, a next-generation intra-operative imaging platform based on real-time multi-spectral image capturing, processing and rendering combined with the use of fluorescence agents is provided. Further details are described in the following with reference to FIGS. 5 and 6.

Figure 5:
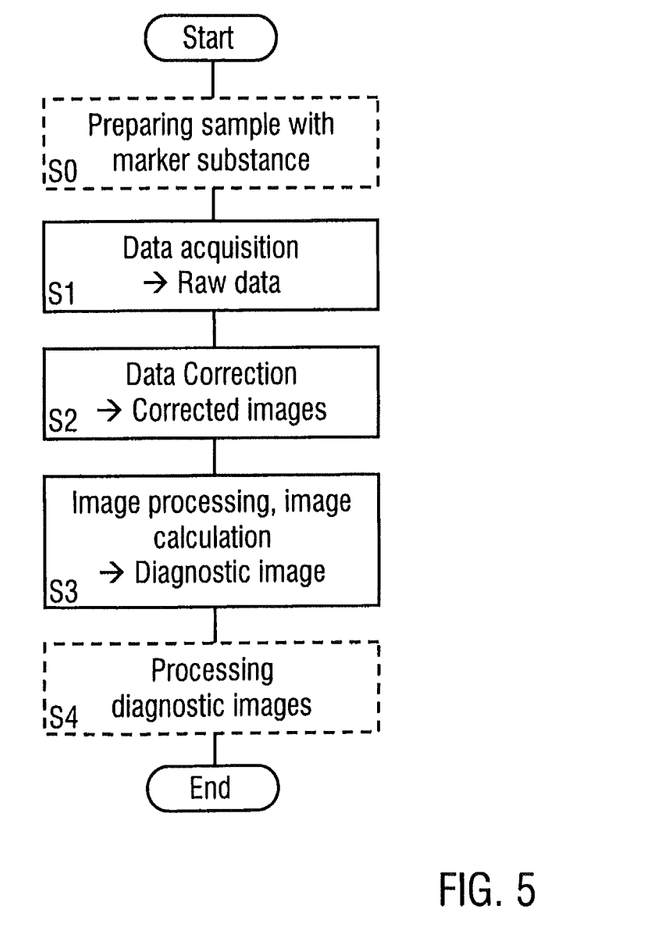
FIG. 5: a flow chart illustrating steps of the imaging method.

FIG. 5 illustrates the steps of the imaging method from data acquisition until calculation of a diagnostic image, comprising preparing the sample with at least one marker substance (S0), data acquisition (including multispectral optical imaging and multispectral opto-acoustic imaging) resulting in raw image data (S1), data correction (including correction for overlapping fluorescence spectra, overlapping absorption spectra, or tissue optical properties such as absorption, scattering, and depth distribution of marker substances) resulting in corrected images of marker substance distribution, like a fluorophore and/or chromophore distribution (S2), an image processing, in particular image calculation (including a combined assessment of multiple marker substances, assessment of temporal characteristics of image signals and/or highlighting particular areas or patterns in a color image) resulting in a diagnostic image (S3), and a further processing of the diagnostic image, like, e.g., image processing, storing, printing, displaying, recording or the like (S4). Steps S1 to S3 represent the essential real-time steps of the imaging method, while steps S0 and/or S4 represent optional features, which can be omitted or conducted at times different from the time of imaging. As an example, the imaging method can be applied with a sample, which already includes the at least one marker substance for natural reasons or due to a preparation in the past.

In more detail, the calculation of images having a diagnostic value, based, e.g., on the color image, the multispectral fluorescence images, the multispectral reflectance images, and opto-acoustic signals can be done conceptually in two stages (see FIG. 5):

(A) Calculate artifact-free fluorescence and reflectance images which represent the spatial distribution of fluorophores and chromophores (step S2).

(B) Use the fluorescence and reflectance images to calculate a diagnostic map of the tissue, i.e., identifying the healthy and diseased tissue (step S3).

(A) Data Correction

Correction procedures applied in real-time are a preferred feature as they lead to artifact-free marker images (i.e., fluorescence images) which accurately represent the spatial distribution of fluorophores or chromophores. Several corrected schemes can be responsible for an integrated correction of all effects that may undergo in a real-time measurement, although a selective number of steps may be applied at specific applications. The generic model considered herein is that the pixel intensity P(x,y) in a raw image is a function of multiple contributions, i.e., $$P(x,y)=f(Pr(x,y), m(x,y,d(x,y)), q(x,y), d(x,y)),$$  Eq. 1 whereby, d(x,y) represents the depths of the marker accumulation, q(x,y) is the contribution of intrinsic signals due to tissue intrinsic fluorochromes and chromophores, m(x,y) is the contribution to the signal of the optical properties in tissue, in particular the attenuation from absorption and scattering, which is also a function of depth and Pr(x,y) is the "real" signal, i.e., the artifact free marker image that is of interest.

In a typical form, Eq. 1 is not linear and solutions can be found with minimizations. However, under certain assumptions, Eq. 1 can become linear, with each term linearly contributing to the raw image. In this case of linear dependence the solution for the "real" image Pr(x,y) can be simply written as:

$$Pr(x,y)=P(x,y)-m(x,y,d(x,y))-q(x,y)-F(d(x,y)),$$  Eq. 2 whereas, F(d(x,y)) herein is a generic function that can correct also for the effects for depth on the signal. The overall correction would also be based on a regression algorithm that identifies the unique spectral components of the "marker" over the contributions or signal alternate from the other contributions. In the following, preferred processing schemes are discussed as implementation examples:

1. Correction of Optical Properties

Variation in light attenuation in tissues can contribute to modifying the signal recorded from the marker. To correct such effects the method teaches of processes that improve on such artifacts. The essence of correction is to independently capture the variation of optical properties and correct the marker signal based on this variation. An example is that varying absorption due to haemoglobin preferentially attenuates fluorescence signals at areas of high absorption, which can lead to artifacts if not corrected.

a) Preferably, multi-spectral measurements are applied to capture the spectral variations of optical attenuation of the illumination, as it appears on the intrinsic (sample light) image. These images can be unmixed in real time to reveal the haemoglobin concentration (by unmixing the oxy- and deoxy-known spectra) and also to reveal scattering by simultaneously fitting for the $1/\lambda^a$ dependence of tissue scattering, where $\lambda$ is the wavelength of measurement and a is a factor that is determined experimentally. Alternatively a time-resolved or frequency resolved camera can be employed for "intrinsic measurements" to independently characterize tissue absorption or scattering.

b) In an alternative example, correction is based on utilizing or adjusting previously known optical measurements by classifying tissue types as identified on the intrinsic images and using this allocation of optical properties to similarly correct the images.

In either case, image correction is based on Eq. 1, the most simplistic form in this case, applied only for corrections for optical properties would take the form:

$$Pr(x,y)=P(x,y)*F(\mu_s'(x,y), \mu_a(x,y))/Pi(x,y)$$  Eq. 3 or more simply $$Pr(x,y)=P(x,y)/g*\mu_s'(x,y)*Pi(x,y)$$  Eq. 4 whereby $\mu_s'(x,y)$, $\mu_a(x,y)$ is the reduced scattering coefficient and absorption coefficient respectively of tissue at each image pixel and Pi(x,y) is an attenuation image (intrinsic image) measured at a spectral region that is identical or close to the one utilized by the fluorescence measurements. In this case Eq. 4 makes use of the fact that the ratio of fluorescence to intrinsic tissue is relatively insensitive to absorption but depends by a factor $3/4\pi$ to the reduced scattering coefficient.

Finally the correction for optical properties can occur simultaneously with correction for depth as described in the following paragraph.

2. Correction for Optical Properties and Depth

When the fluorophore is covered by a thin layer of tissue, then the fluorescence signal depends on the optical properties of the overlaying tissue in a dual way:

(a) the excitation light, typically monochromatic, is attenuated by absorption and scattering so that only a portion of light reaches the fluorescence marker and induces fluorescence, and (b) the emitted fluorescence is also attenuated while propagating through the tissue. The fluorescence light, typically broadband, undergoes different degree of attenuation for every wavelength depending on the absorption and scattering properties of the tissue.

Nevertheless, absorption in tissue is predominately due to hemoglobin (oxy- and deoxy-) which have specific, well known absorption spectra. Similarly, tissue scattering spectrum has relatively small variations in shape. Therefore, when the fluorescence light diffuses through a thin layer of tissue, its spectrum is altered in a characteristic way depending on the thickness and the concentration of absorbers and scatterers within the overlaying tissue layer. Multispectral measurement of the fluorescence signal can reveal these spectral alterations and correct them.

The measured fluorescence signal, i.e., S, is a function of some parameters:

$$S(x,y,\lambda) = F(C_m(x,y,d), OP_m(\lambda), C_k(x,y,d), OP_k(\lambda), I_{ex}(x,y,d)) \quad \text{Eq. 5}$$

whereby $C_m(x,y,d)$ and $OP_m(\lambda)$ are the concentration and the optical properties of the fluorescence marker respectively. $C_k(x,y,d)$ and $OP_t(\lambda)$ are the concentration and the optical properties of tissue chromophores, fluorophores and scatterers that consist the tissue layer, e.g., k=3 oxy-, deoxy-hemoglobin and total tissue scatterers, d is the depth of the fluorescence marker or equivalently the thickness of the overlaying tissue and consequently, $I_{ex}(x,y,d)$ is the intensity of excitation light reaching the fluorescence marker at depth d and depends on tissue optical properties:

$$I_{ex}(x,y,d) = I_0 * G(C_k(x,y,d), OP_k(\lambda)) \quad \text{Eq. 6}$$

whereby, $I_0$ is the intensity of excitation light illuminating the tissue under examination.

The optical properties, i.e., absorption, scattering and fluorescence spectra of the tissue components and the fluorescence marker, $OP_t(\lambda)$ and $OP_m(\lambda)$, are known and can be used as priors. Measurements of the fluorescence signal at multiple wavelengths ($\lambda_i$, i=1,2, ... n) will result in a system of n equations (Eq. 5) where n≥k+1. The solution of this system of equations results in the actual concentration of the fluorescence marker $C_m(x,y,d)$ but also the optical properties of the tissue layer, i.e., $C_k(x,y,d)$. Thereby, the fluorescence signal originating from sub-superficial layer is corrected for tissue optical properties and depth of the marker.

3. Overlapping of Fluorescence Spectra/Auto-Fluorescence Correction

To enable simultaneous measurement of multiple probes, i.e., marker molecules that mark multiple targets, and also for retrieving potentially wanted or unwanted signal contributions coming from background intrinsic molecules (i.e., intrinsic chromophores, fluorochromes and the like) background it is a common practice to perform spectral unmixing of known or potentially even unknown contributions. Due to the general wide spectral contributions of tissue and external fluorochromes there may be significant spectral overlapping that cannot be otherwise resolved unless with spectral unmixing techniques (blind or deterministic) or similarly linear regression for match the spectral measurements measured to the assumed background contributions.

(B) Image Calculation

Although, artifact free fluorescence and reflectance images can accurately provide the spatial distribution of fluorescence probes and tissue chromophores, it is not always straight forward to conclude if a tissue area is diseased or not. The diagnostic capability of each diagnostic probe is based on targeting a characteristic difference of the disease compared to healthy tissue. Nevertheless, diseases like cancer exhibit a remarkable variability in their characteristics and therefore, a single probe targeting a single cancer feature is often not very specific. By combined evaluation of multiple cancer features by means of multiple probes, can provide significantly increased specificity and sensitivity. Additionally, automatic fusion of the diagnostic information with the color image of the tissue under examination provides a convenient and easy to use modality, suitable for clinical use.

FIG. 6 illustrates another example of a two channel imaging device 100 for intraoperative fluorescence imaging. The imaging device 100 in particular comprises a light source 11, e.g., a halogen lamp, and a notch filter 12 to illuminate a sample 1; a light splitting imaging optic 30 with an imaging optic 31.1, e.g., a zoom lens, relay lenses 31.2, and an image splitter 33, e.g., a plate beam splitter with 10% reflectance and 90% transmittance; a sample light camera 21 having a visible light filter 34; and a marker light camera having a narrow band pass filter 35.

The system of FIG. 6 is capable of measuring simultaneously, color, fluorescence and intrinsic (excitation wavelength) images for marker substances (fluorescence probes) emitting in the near infrared region. Nevertheless, if the emission spectrum of the fluorescence probe falls well within the visible range, e.g., FITC, then the simultaneous measurement of fluorescence and reflectance is not possible with the same configuration.

FIG. 6 further illustrates a method that allows simultaneous capturing color reflectance image and visible fluorescence. This method is based on the combination of the notch filter 12 and the complimentary narrow band pass filter 35 of the marker light camera 22. The notch filter 12 blocks a narrow spectral band and transmits the rest. In this setup, the light from the white light source 11 is filtered using a 532 nm notch filter. Thereby, the same light source can be used for both white light illumination and fluorescence excitation. Light collected by the imaging optic 31 is split in two imaging channels, for visible and fluorescence measurements. The fluorescence channel employs a complementary to the notch filter, narrow band pass filter 35. Thereby, only the fluorescence light reaches the marker light camera 22 as all the reflected light is rejected by the band pass filter. In analogy to the preceding paragraphs, this implementation correction for optical properties comes from processing the at least two spectral bands provided by camera 21 (a color camera in a preferred example).

Figure 7:
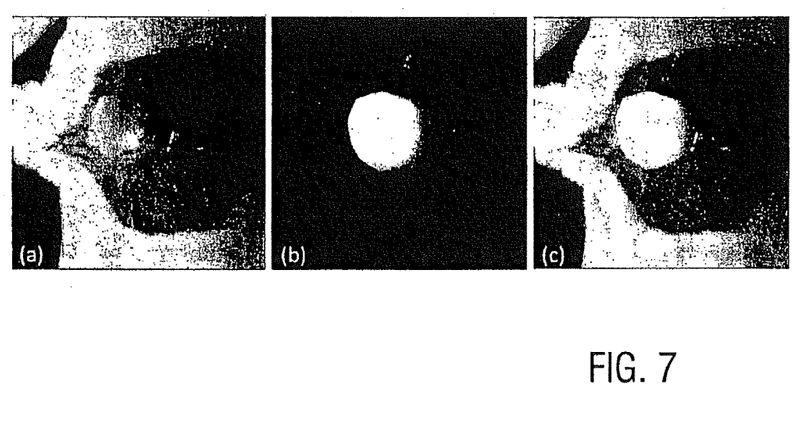
FIGS. 7 and 8: photographs illustrating experimental results.

FIG. 7 shows images (photographs) captured using the imaging device of FIG. 6. FIG. 7a shows the color image collected with the sample light camera 21, FIG. 7b shows the fluorescence image at 532 nm collected with the marker light camera 22, and FIG. 7c shows a pseudocolor image resulted from a fusion of images 7a and 7b. Even with the black-and-white-representation presented here for technical reasons, the essential advantage of the fused image 7c over the color image 7a is clearly demonstrated.

Figure 8:
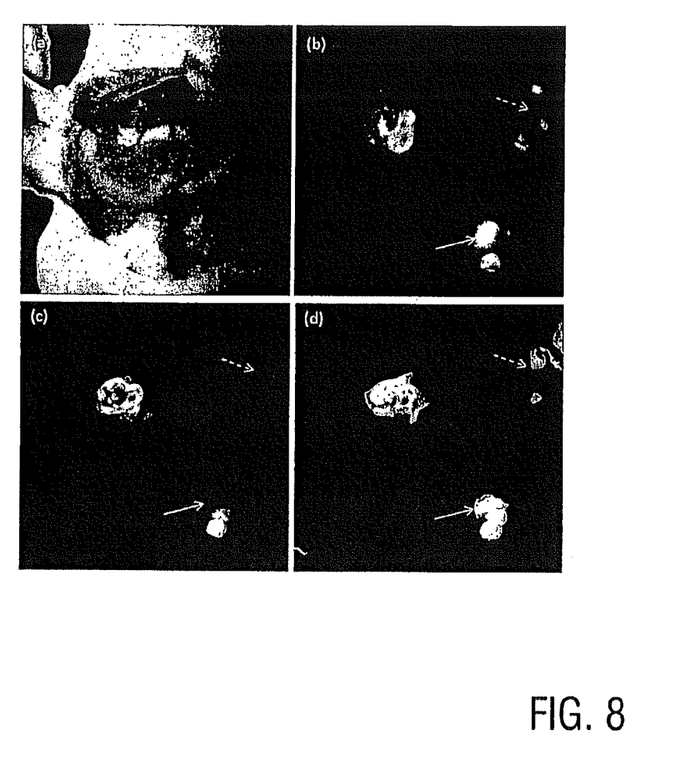

FIG. 8 shows images of a mouse with intra-peritoneal tumors. FIG. 8a shows a reflectance color images which illustrates the anatomical features of the animal's body. FIG. 8b shows a bioluminescence image which reveals the tumor spots. The bioluminescence image is used here as a reference image which accurately reveals the exact tumor location and size. FIG. 8c shows a fluorescence image at 716 nm originating from a diagnostic fluorescent marker injected prior to imaging session. Raw fluorescence signal does not illustrate one of the tumor spots at the upper-right part of the image, indicated with a dashed arrow, and also does not reveal correctly the size of a second spot at the lower-right part of the image, indicated with an arrow. FIG. 8d shows a corrected fluorescence image where all the tumor spots are illustrated correctly. The correction of the fluorescence image (marker light signal) was performed using the reflectance spectral images (sample light signals) which are not shown in FIG. 8.

Figure 9:
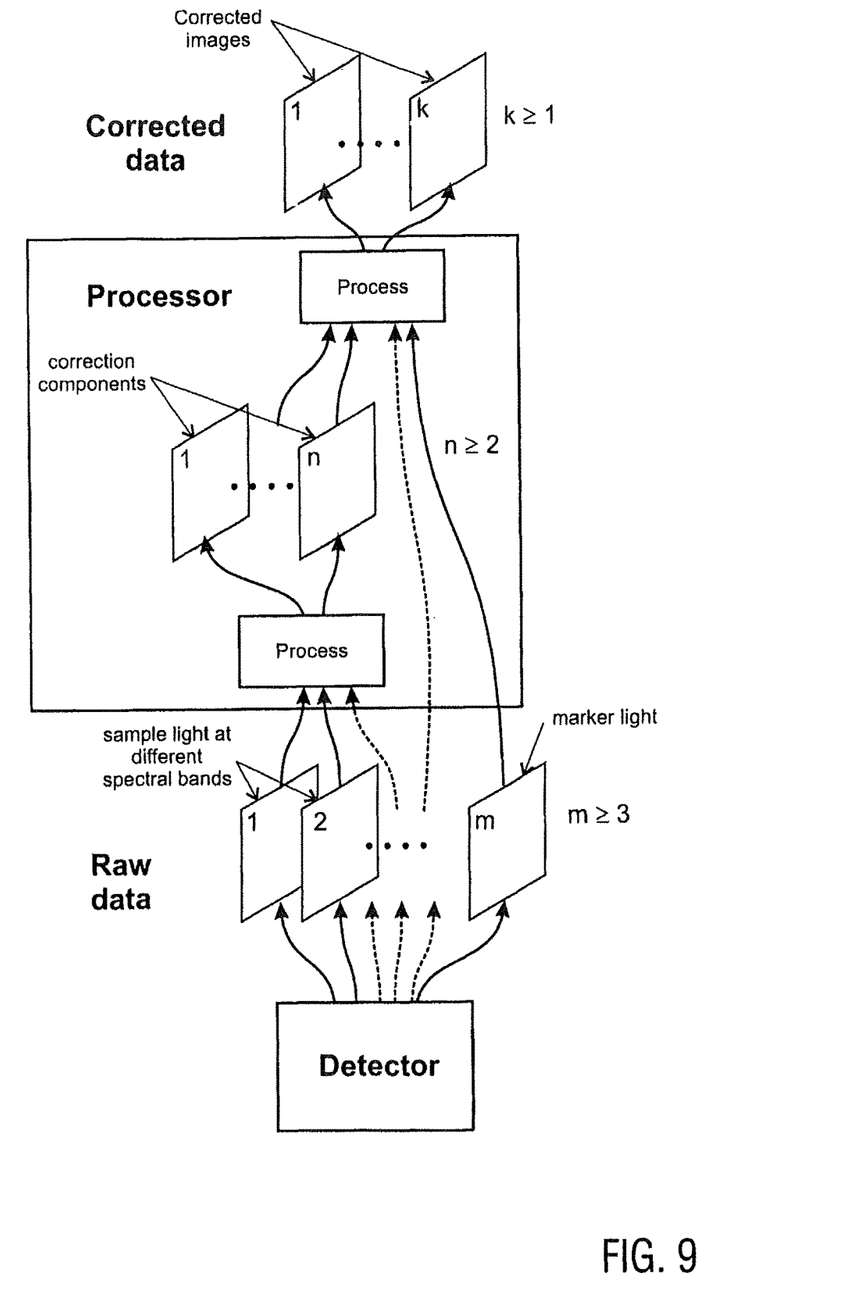
FIG. 9: a schematic illustration of the function of the imaging device according to one example of the device.

FIG. 9 shows a schematic of the function of an example of the imaging device.

According to FIG. 9, the detector may include a combination of optical and opto-acoustic sensors and detects signals originating from the examined sample. The output of the detector is at least 3 images which are:
- at least two images of sample light, captured at different spectral bands, and
- at least one image of marker light (e.g., fluorescence).

The images captured by the detector, are processed by a processor. The processing can be done in two stages:
a. the at least two sample light images are processed to produce at least two correction components, e.g., correction images. These correction components could relate to the optical properties of the sample, e.g., absorption and scattering.
b. the at least one marker light image, e.g., fluorescence image, is processed using at least the two correction components calculated in process (a). This process calculates at least one corrected marker light image.

The processor could also perform other processes like combining the two correction components into one, which is then used to correct the marker light image or utilize opto-acoustic data to yield further information on absorption for more accurate correction. The output of the processor is at least one corrected marker light image.

The features disclosed in the above description, the drawings and the claims can be of significance both individually as well as in combination for the realization of the device and method and variations thereof.

The invention claimed is:

1. An imaging device comprising:
(a) a light source device arranged to illuminate a sample under investigation with illumination light, said light source device including a narrowband light source arranged to excite a marker fluorescence from at least one marker substance in the sample and a broadband light source arranged to illuminate the sample,
(b) a detector device including at least one multi-spectral sample light camera and at least one marker light camera and being arranged to collect a plurality of images in response to said illumination with the narrowband light source and the broadband light source, said plurality of images including:
at least two sample light images reflected by the sample in different spectral ranges, and
at least one marker light image originating from at least one marker substance in the sample, wherein the at least one sample light camera is provided with an optical filter which is arranged for passing visible light for adjusting the spectral ranges of the sample light reflected by the sample,
wherein
a light splitting imaging optic is provided which is configured for imaging light from the sample onto the cameras by relaying sample light onto the at least one sample light camera and marker light onto the at least one marker light camera so that both of the sample light and the marker light are collected simultaneously, and
(c) a processor device adapted to process the at least two sample light images and create at least one correction component from the at least two sample light images, the processor device further adapted to correct the marker light image using the at least one correction component.

2. The imaging device according to claim 1, wherein the processor device processes the sample and marker light images and renders at least one of the processed images in real-time.

3. The imaging device according to claim 1, wherein the detector device is arranged to collect the at least two marker light images at different spectral bands.

4. The imaging device according to claim 3, wherein the processor device uses at least two marker light images to correct the marker light image for autofluorescence originating from the sample.

5. The imaging device according to claim 1, wherein the processor device calculates the at least one correction component from the sample light images captured in red, green and blue regions of the light spectrum.

6. The imaging device according to claim 1, wherein the processor device processes the at least two sample light images to produce at least two correction components which are then used for correction of the marker light image and rendering at least one corrected marker light image in a real-time mode.

7. The imaging device according to claim 1, wherein the processor device processes the at least two sample light images to produce at least one correction component which is primarily associated with absorption properties of the sample and at least one correction component which is primarily associated with scattering properties of the sample.

8. The imaging device according to claim 1, wherein the processor device performs the correction of the marker light image using any combination of the following correction components:
a correction component which is primarily associated with absorption properties of the sample,
a correction component which is primarily associated with scattering properties of the sample,
a correction component which is primarily associated with autofluorescence of the sample,
a correction component which is primarily associated with spatial characteristics of illumination,
a correction component which is primarily associated with depth distribution of the marker.

9. The imaging device according to claim 1, wherein the processor device reassembles the at least two correction components into one correction component which is then used to correct the marker light image.

10. The imaging device according to claim 1, wherein:
the sample and marker light images are collected with at least two imaging channels, wherein each imaging channel includes at least one optical filter and at least one imaging detector.

11. The imaging device according to claim 1, wherein the light source device includes at least one illumination light conditioning device that adjusts at least one of a spectral characteristic, a temporal characteristic, a polarization, a direction and a light field shape of the illumination light.

12. The imaging device according to claim 1, wherein the at least one illumination light conditioning device comprises at least one of a spectral filter, a polarization filter, an illumination optic and a bundle of optical fibers.

13. The imaging device according to claim 1, further comprising an opto-acoustic imaging device arranged to collect an opto-acoustic image of the sample.

14. The imaging device according to claim 13, wherein the processor device uses the opto-acoustic image for at least one of the following procedures:
    processing the opto-acoustic image to produce at least one additional correction image which then used for correction of the marker light image,
    displaying the opto-acoustic image of the sample, and
    reassembling the opto-acoustic image with the corrected optical image into one image and rendering that image in a real-time mode.

15. The imaging device according to claim 1, further comprising a control device including at least one:
    the control device is configured to control at least one of the light source device, the detectors and the processor device in real time,
    the control device is connected with a display device displaying the at least one of the sample light images, marker light image, correction image, corrected marker light image, opto-acoustic image or a combination thereof in real time, and
    the control device is connected with an administering device configured to introduce at least one predetermined marker substance into the sample.

16. The imaging device according to claim 1, wherein the processor device includes at least one of Field Programmable Gate Arrays and Graphic Processing Units.

17. The imaging device according to claim 1, wherein detectors of the detector device are arranged with a modular structure having a plurality of couplings each of which is arranged to accommodate one of the detectors.

18. The imaging device according to claim 1, which is a medical imaging device.

19. An imaging method, wherein the imaging device comprising:
    (a) a light source device arranged to illuminate a sample under investigation with illumination light, said light source device including a narrowband light source arranged to excite a marker fluorescence from at least one marker substance in the sample and a broadband light source arranged to illuminate the sample,
    (b) a detector device including at least one multi-spectral sample light camera and at least one marker light camera and being arranged to collect a plurality of images including:
        at least two sample light images reflected by the sample in different spectral ranges, and
        at least one marker light image originating from at least one marker substance in the sample, wherein
        the at least one sample light camera is provided with an optical filter which is arranged for passing visible light for adjusting the spectral ranges of the sample light reflected by the sample,
    wherein
    a light splitting imaging optic is provided which is configured for imaging light from the sample onto the cameras by relaying sample light onto the at least one sample light camera and marker light onto the at least one marker light camera so that both of the sample light and the marker light are collected simultaneously, and
    (c) a processor device adapted to process the at least two sample light images and create at least one correction component from the at least two sample light images, the processor device further adapted to correct the marker light image using the at least one correction component,
    the method comprising:
        illuminating a sample under investigation with illumination light generated with the light source device,
        collecting at least two sample light images from sample light reflected by the sample in different spectral ranges,
        collecting at least one marker light image from marker light generated by at least one marker substance in the sample, and
        processing the sample and marker light images and rendering at least one corrected marker light image based on the at least two sample light images and the at least one marker light image.

20. The imaging method according to claim 19, further comprising at least one of:
    rendering the at least one corrected marker light image in a real-time mode,
    adjusting at least one of a spectral characteristic, a temporal characteristic, a polarization, a direction and a light field shape of the illumination light,
    adjusting a spectral or temporal sensitivity of each of the sample light and marker light cameras, and
    collecting an opto-acoustic image of the sample with an opto-acoustic imaging device.

21. The imaging method according to claim 19, wherein the sample includes at least one of:
    the sample comprises biological tissue, and
    the sample includes multiple marker substances having different spectroscopic properties.

22. The imaging method according to claim 19, which performs medical imaging.

23. The imaging method of claim 1, wherein the medical imaging is associated with intra-operative, laparoscopic or endoscopic applications.

* * * * *